United States Patent [19]

Tan et al.

[11] Patent Number: 4,675,370

[45] Date of Patent: Jun. 23, 1987

[54] RESIN SYSTEMS DERIVED FROM BENZOCYCLOBUTENE-ALKYNE IMIDE MONOMERS

[75] Inventors: Loon-Seng Tan; Fred E. Arnold, both of Centerville, Ohio

[73] Assignee: University of Dayton, Dayton, Ohio

[21] Appl. No.: 857,008

[22] Filed: Apr. 29, 1986

[51] Int. Cl.[4] .............................................. C08F 38/00
[52] U.S. Cl. ...................................... 526/259; 546/83; 546/114; 546/115; 548/118; 548/224; 548/303
[58] Field of Search ................... 526/259, 280; 546/83, 546/114, 115; 548/118, 224, 303; 585/27

[56] References Cited

U.S. PATENT DOCUMENTS 3,609,160  9/1971  Meyer ................................. 548/224
4,540,763  9/1985  Kirchhoff ........................... 526/284
4,570,011  2/1986  So ....................................... 560/8

Primary Examiner—Paul R. Michl
Attorney, Agent, or Firm—Biebel, French & Nauman

[57] ABSTRACT

Resins are obtained by Diels-Alder polymerization of a monomer of the formula

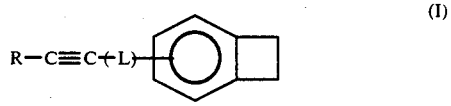

(I)

where
R is a hydrogen atom or an aryl group; and
L is an aromatic linking group.

27 Claims, 3 Drawing Figures

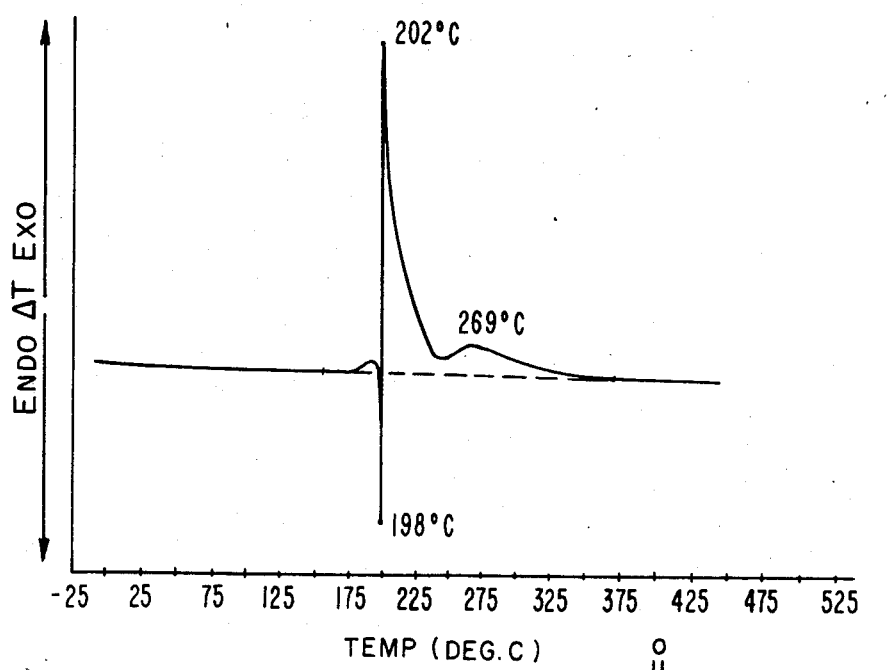
FIG. 1 DSC of 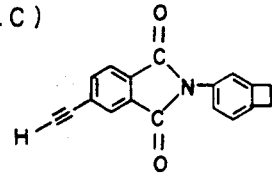
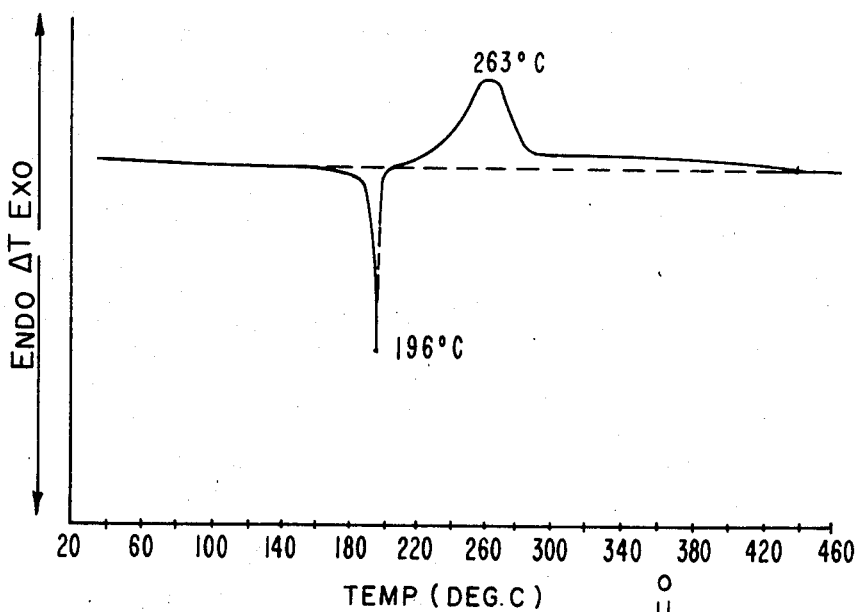
FIG. 2 DSC of 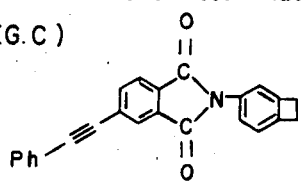

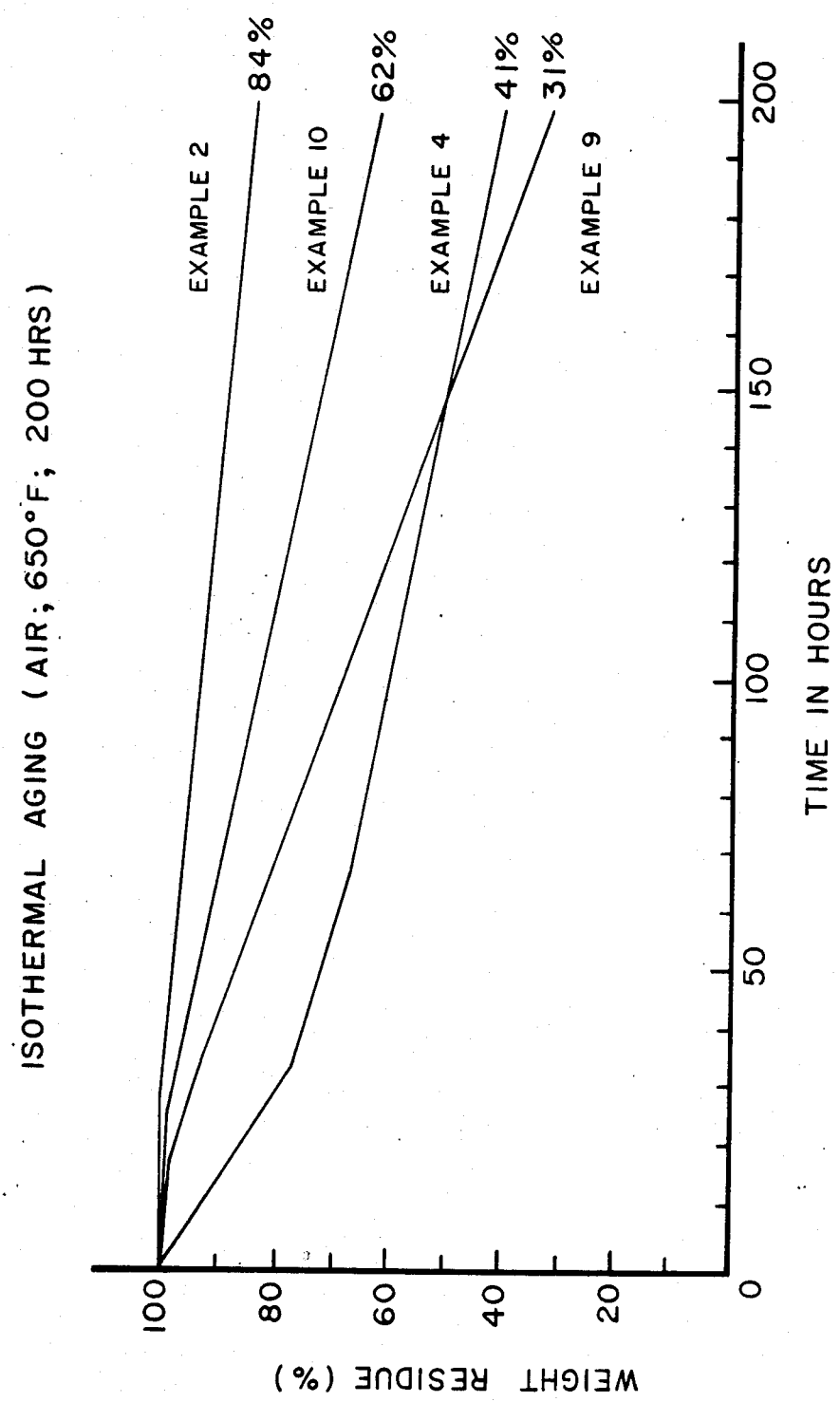

RESIN SYSTEMS DERIVED FROM BENZOCYCLOBUTENE-ALKYNE IMIDE MONOMERS

The U.S Government has rights in this invention pursuant to contract No. F33615-84-C-5020 awarded by the Department of the Air Force.

BACKGROUND OF THE INVENTION

The present invention relates to resins obtained by Diels-Alder polymerization, and more particularly, to high temperature tolerant thermoset resins obtained by Diels-Alder polymerization of benzocyclobutene-alkyne imide monomers The Diels-Alder reaction is a cycloaddition reaction in which an unsaturated group, which is a dienophile, combines with a 1,3-diene to form a six membered ring. The Diels-Alder reaction appears to be favored by the presence of the diene's electron-yielding groups, and the dienophile's electron-attracting groups. Although the Diels-Alder reaction is used extensively in organic chemistry, it is less commonly employed in polymer chemistry. At high temperatures, most Diels-Alder adducts undergo conversion to other products, such as aromatic rings, before the temperature required for the reverse reaction is reached; consequently, most Diels-Alder polymers exhibit high thermal stability.

In most Diels-Alder polymerizations, a bisdiene reacts with a bisdienophile. For example, in W. J. Bailey et al., "Polymeric Diels-Alder Reactions," *J. Org. Chem.* 27, 3295 (1962), 2-vinylbutadiene, a bifunctional diene, is reacted with benzoquinone, a dienophile. J. K. Stille, "Cycloaddition Polymerization," *Die Makromolekulare Chemie* 154,49 (1972), teaches that cyclopentadienones undergo a variety of Diels-Alder reactions depending on the ring substitution, dienophile, and reaction conditions. To obtain a monoadduct, cyclopentadienone is employed with an acetylenic dienophile to obtain an aromatic product. Additionally, R. T. Kohl et al., "Diels-Alder Reactions of Phenyl-Substituted 2-Pyrones: Direction of Addition with Phenylacetylene," *Macromolecules* 11,340 (1978) shows the Diels-Alder reactions of substituted acetylenes with 2-pyrones. J. N. Braham et al., "Polyphenylenes via Bis (2-pyrones) and Diethynylbenzenes, The Effect of m- and p-Phenylene Units in the Chain," *Macromolecules* 11,343 (1978) shows the Diels-Alder 4+2 cycloaddition reaction of bis (2-pyrone) monomers with diethynylbenzenes.

In some Diels-Alder polymerizations, the same molecule contains both a diene and a dienophile moiety. W. J. Bailey, "Diels-Alder Polymerization," *Step-Growth Polymerization*, Marcel Dekker, New York, 1972, stresses that this type of polymerization presents considerable difficulty. One class of monomer is capable of functioning as both a diene and a dienophile. Cyclopentadiene and 2-vinylbutadiene are two examples. In another class of monomer, the diene and dienophile are different. Meek and Argabright, *J. Org. Chem.* 22, 1708 (1957) prepared 6-[p-(p-maleimidobenzoyloxy)-phenyl]-1,2,3,4-tetrachlorofulvene which contains a maleimido group as a dienophile and a perchlorofulvene group as a diene.

Bis-benzocyclobutenes and polymers derived therefrom are disclosed in U.S. Pat. No. 4,540,763. The bis-benzocyclobutenes are connected by direct bond or a bridging member such as a cyclic imido group. In general, the polymers are obtained by addition polymerization wherein the fused cyclobutene rings undergo thermal transformation to an o-xylylene moiety which can react with one another.

SUMMARY OF THE INVENTION

An object of the present invention is to provide monomers which are polymerizable by Diels-Alder polymerization.

Another object of the present invention is to provide monomers useful in the preparation of high-temperature tolerant thermoset resins by Diels-Alder polymerization.

A more particular object of the present invention is to provide high-temperature tolerant thermoset resins prepared by Diels-Alder polymerization of benzocyclobutene-alkyne imide monomers.

An additional object of the present invention is to provide high-temperature tolerant thermoset resins which are useful in composites and as adhesives.

In accordance with the present invention, resins are obtained by the Diels-Alder polymerization of monomers which exhibit both diene and dienophile functionalities. The present invention provides monomers of the general formula (I)

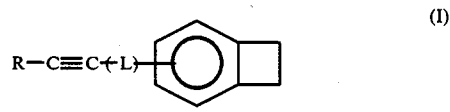

wherein R is a hydrogen atom or an aryl group; and L is an aromatic linking group. Upon heating these monomers to about 200° C., the benzocyclobutene unit undergoes an electrocyclic ring-opening to form the more reactive o-xylylene functionality. 0-xylylene is a powerful diene, and thus, engages in a Diels-Alder polymerization with the alkyne unit of the molecule.

In one embodiment, the monomer is represented by the formula (Ia)

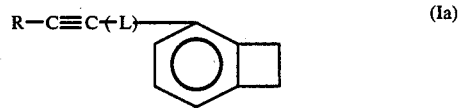

and R and L are defined as in formula (I) above. In another embodiment, the monomer is represented by the formula (Ib)

and R and L are defined as in formula (I) above.

In the monomer of formula (I) above, careful attention must be paid to the selection of the R moiety. R is selected such that the dienophile exhibits sufficient stability up to the in situ generation of o-xylylene. Alkynes can polymerize by themselves at sufficiently high temperatures; thus, R is selected such that homopolymerization of the alkyne will not detract from the product of the Diels-Alder reaction. Stated differently, upon heating the monomers of the present invention, homopolymerization of the alkyne and Diels-Alder polymerization of the diene and the alkyne can both occur. R is selected such that homopolymerization of the alkyne does not detract from the properties desired in the Diels-Alder product. In a preferred embodiment of the present invention, R is a hydrogen atom or an aryl group. In a more preferred embodiment, R is a phenyl group.

There are thermodynamic feasible pathways to convert the six-membered rings formed by the Diels-Alder polymerization (in particular, the ones that are fused to an aromatic nucleus or linked to electron-withdrawing groups such as carbonyl groups) to highly thermally stable structures. Hence, to maximize the thermal stability of the resin, in the monomer of formula (I) above, L is selected so as to provide a linking group which is as thermooxidatively stable as the Diels-Alder polymerization bond. Thus, in one embodiment, L is an aromatic linking group, and more particularly, a benzimido group. In other applications where thermooxidative stability is not as critical, numerous L groups are useful in the monomer of the present invention.

In one embodiment, L is represented by the formula selected from the group consisting of

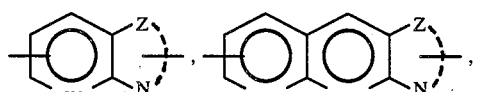

(II) (III)

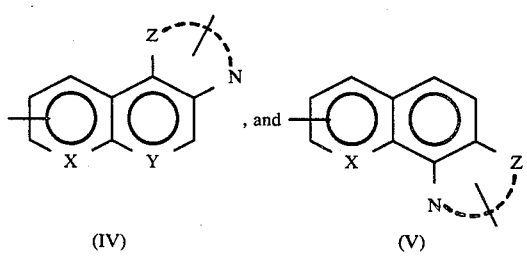

(IV) (V)

where
W, X, and Y are a hydrogen atom or a nitrogen atom; and
Z represents the atoms necessayr to complete a nitrogen containing heterocyclic ring selected from the group consistng of an imidazole ring, an oxazole ring, and a thiazole ring.

In another embodiment, L is represented by the formula (VIII)

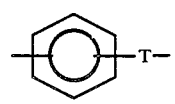

(VIII)

where T is selected from the group consisting of

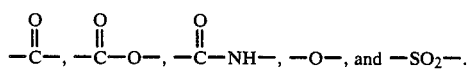

In an additional embodiment, L is represented by the formula (IX)

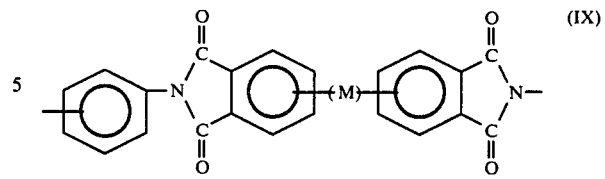

(IX)

where M is selected from the group consisting of —C(CF$_3$)$_2$—, —C(CH$_3$)$_2$—, and

In another embodiment, L is represented by the formula (X)

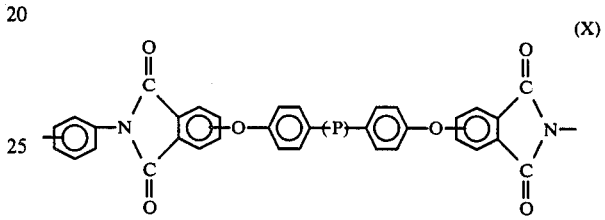

(X)

where P is selected from the group consisting of —SO$_2$—, —C(CF$_3$)$_2$—, and —C(CH$_3$)$_2$—.

In a particularly preferred embodiment, L is a benzimido group represented by the formula (VI)

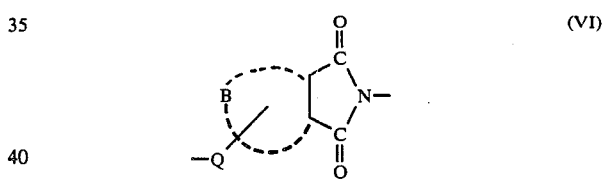

(VI)

where
B represents the atoms necessary to complete a condensed benzene ring or a condensed napthalene ring; and
Q is a direct bond or a moiety of the formula (VII)

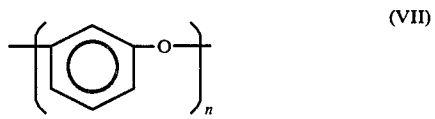

(VII)

where n is 1 or 2. In the preferred embodiments, B represents a condensed benzene ring and Q is at the 4-position as shown in formula (VIa)

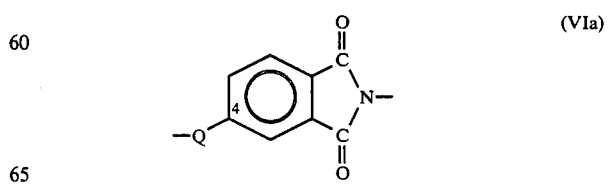

(VIa)

Some resins with excellent high temperature stability are obtained by Diels-Alder polymerization of monomers of the formula (I) above where L is represented by the formula (VI) above.

BRIEF DESCRIPTION OF THE DRAWINGS

FIG. 1 is a DSC curve for a monomer of formula (I) where: R is a hydrogen atom, and L is represented by the formula (VI) where B is a benzene ring and Q is a direct bond.

FIG. 2 is a DSC curve for a monomer of formula (I) where: R is a phenyl group, and L is represented by the formula (VI) where B is a benzene ring and Q is a direct bond.

FIG. 3 provides isothermal aging studies for four monomers of formula (I).

DETAILED DESCRIPTION OF THE INVENTION

Table 1 contains examples of L where L is represented by formula (II).

TABLE 1

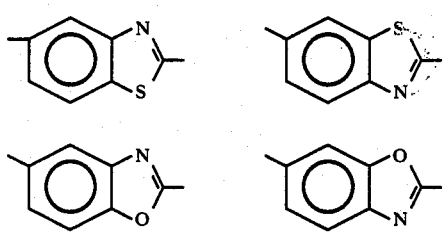

TABLE 1-continued

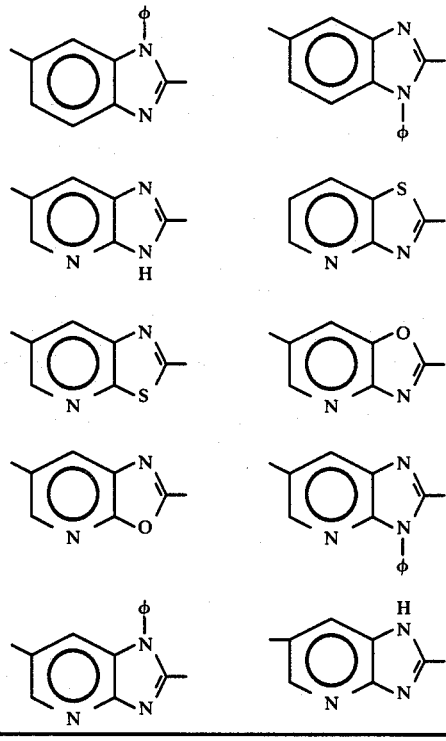

Table 2 contains examples of L where L is represented by the formula selected from the group consisting of (III), (IV) and (V).

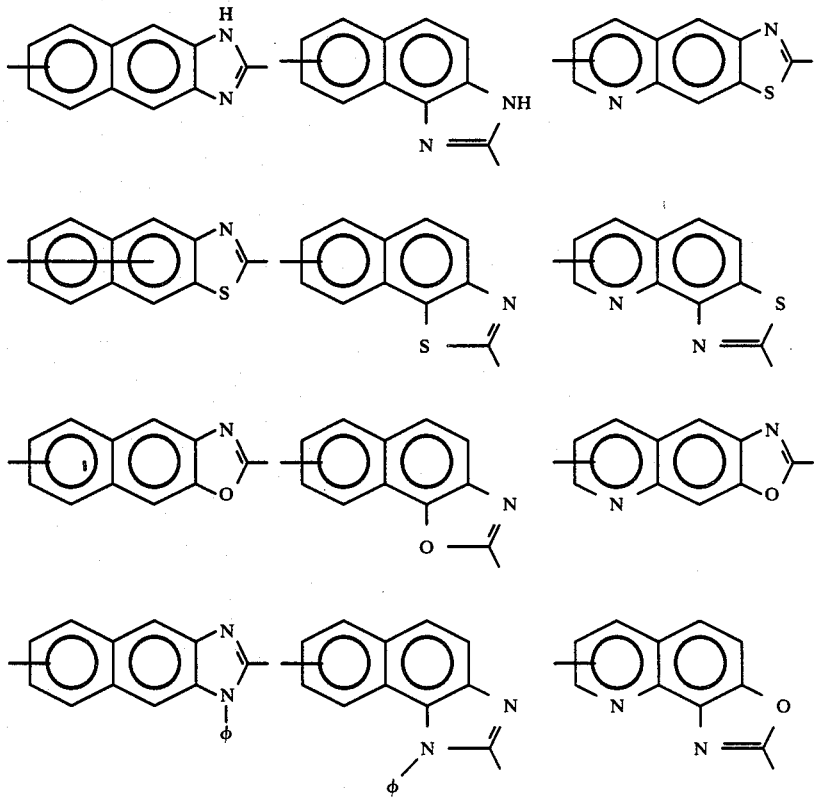

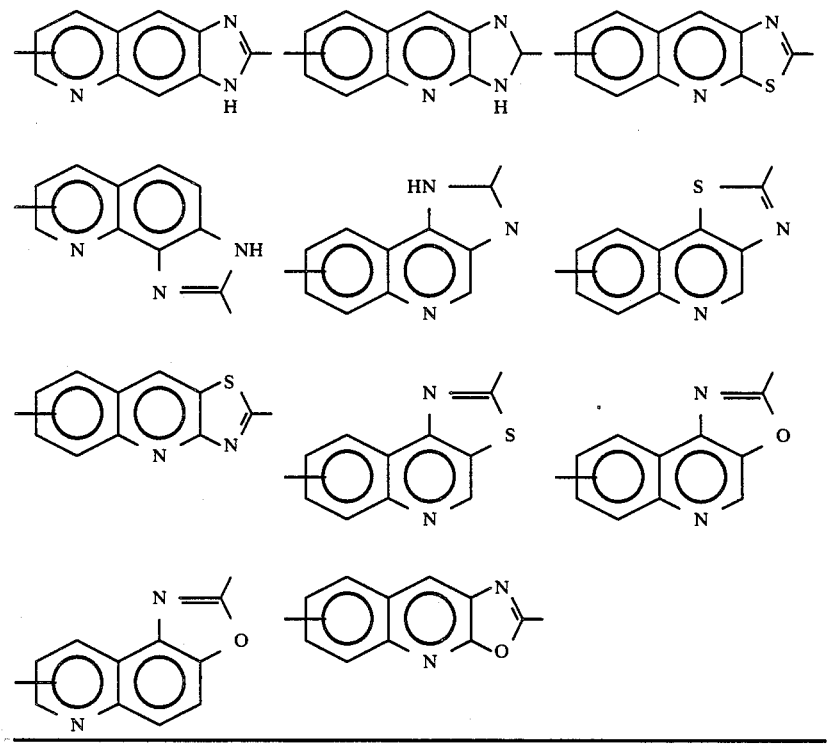
Table 3 contains examples of L where L is represented by the formula (VIII).
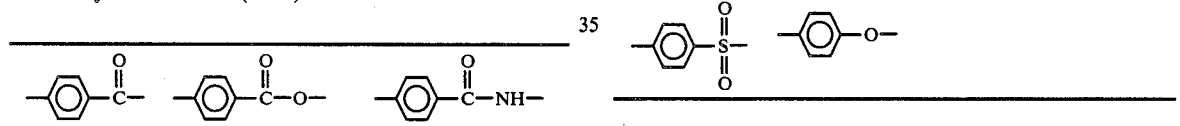
Table 4 contains examples of L where L is represented by the formula selected from the group consisting of (IX) and (X).
TABLE 4
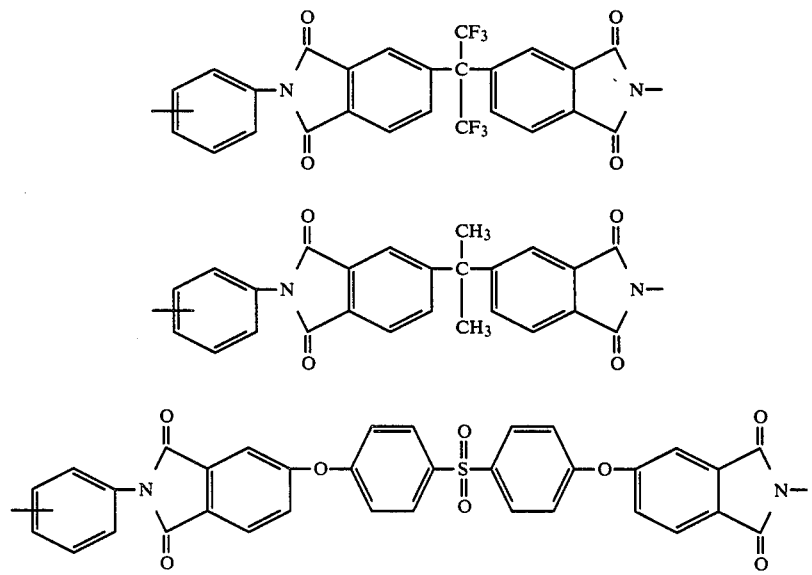

TABLE 4-continued

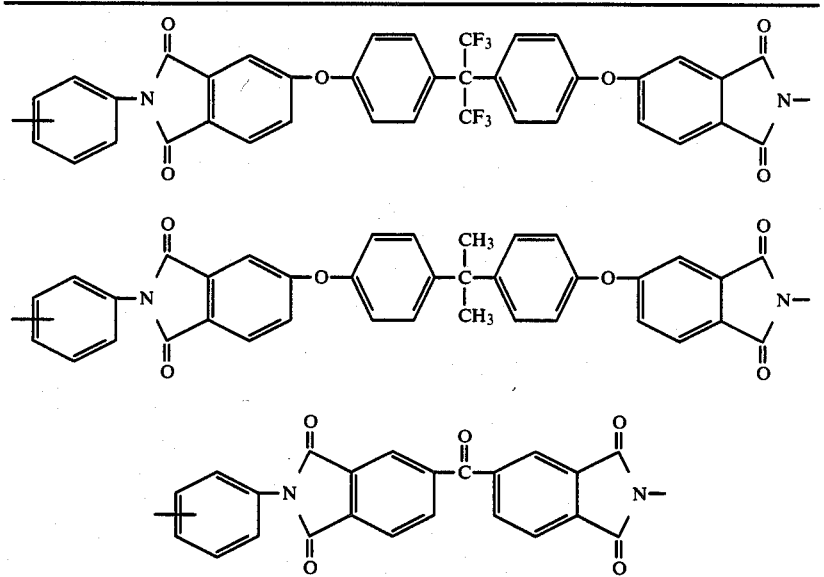

The benzocyclobutene-alkyne imide monomers useful in this invention can be prepared by several synthesis schemes. The preferred methods of preparation of such monomers are described hereinafter.

To prepare a monomer of the formula (I) wherein L is represented by the formula (II), an amine of the formula

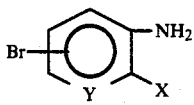

and benzocyclobutene-4-carboxylic acid are reacted in polyphosphoric acid at about 150° C. to form the condensation product. Subsequent reaction of the condensation product and phenylacetylene in the presence of a palladium catalyst using triethylamine as the solvent (catalytic ethynylation) results in the formation of the desired phenylacetylene-benzocyclobutene monomer. A monomer of the formula (I) wherein L is represented by the formula selected from the group consisting of (III), (IV), and (V) is prepared similarly according to the foregoing synthetic scheme.

To prepare a monomer of the formula wherein L is represented by the formula (VIII) and T is

a bromo-benzoic acid chloride and benzocyclobutene are reacted in the presence of aluminum chloride in nitrobenzene (Friedel-Crafts Reaction) to form a bromophenyl benzocyclo-butenyl ketone. Catalytic ethynylation of the ketone with phenylacetylene in the presence of palladium catalyst using triethylamine as the solvent results in the formation of the desired phenylacetylene-benzocyclobutene monomer. To prepare a monomer of the formula (I) wherein L is represented by the formula (VIII) and T is —SO₂—, the bromobenzene sulfonyl chloride is reacted in place of the benzoic acid chloride.

To prepare a monomer of the formula (I) wherein L is represented by the formula (VIII) and T is

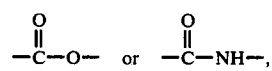

a bromobenzoic acid chloride and either 4-aminobenzocyclobutene or 4-hydroxybenzocyclobutene are reacted to form the ester or amide. Subsequent catalytic ethynylation of the ester or amide with phenylacetylene in the presence of a palladium catalyst and using triethylamine as the solvent results in the formation of the desired phenylacetylene-benzocyclobutene monomer.

To prepare a monomer of the formula (I) wherein L is represented by the formula (VIII) and T is —O—, Ullman ether reaction of 2-bromobenzaldehyde and 4-hydroxybenzocyclobutene in the presence of a suitable base and a copper catalyst results in the formation of an ether of the formula

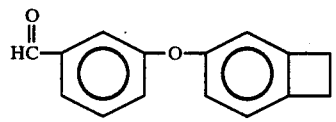

Subsequent treatment of the ether with 1 equivalent of bromomethyltriphenylphosphonium bromide and 2 equivalents of potassium t-butoxide in tetrahydrofuran at −78° C. leads to the formation of an acetylene of the formula

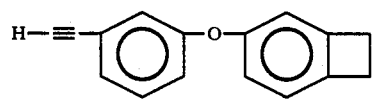

Catalytic ethynylation of the acetylene results in the formation of the desired phenylacetylene-benzocyclobutene monomer.

To prepare a monomer of the formula (I) wherein L is represented by the formula selected from the group consisting of (IX) and (X), a dianhydride of the formula

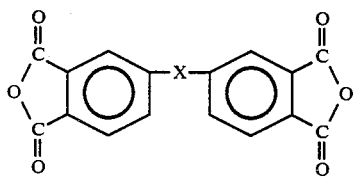

and aminotolane (ortho, meta or para) are reacted in a 1:1 stoichiometric amount and in an appropriate solvent to form

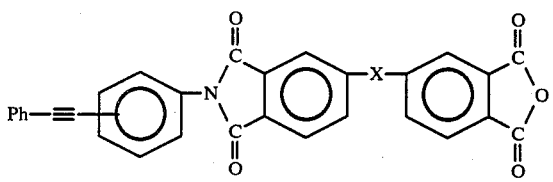

as the major product. Subsequent reaction with 4-aminobenzocyclobutene results in the formation of the desired phenylacetylene-benzocyclobutene monomer.

The methods of preparation of the preferred benzocyclobutene-alkyne imide monomers of the present invention wherein L is represented by the formula (VI) above are described in the examples below.

In general, the resins of the present invention are prepared by Diels-Alder polymerization of the particular monomers used. Upon heating the monomers to about 200° C, Diels-Alder polymerization occurs whereby the benzocyclobutene unit undergoes an electrocyclic ring-opening to form the more reactive o-xylylene functionality wherein the o-xylylene functionality undergoes cycloaddition with the alkyne functionality. Homopolymerization of the alkyne functionality can occur simultaneously with the Diels-Alder polymerization. Hereinafter, "homopolymerization" refers to polymerization of the alkynyl functionality with itself. In preparing the resins of the present invention, however, the Diels-Alder polymerization has to occur at a substantially greater rate than the homopolymerization in order to maximize the thermal stability of the resins.

In a monomer of the formula (I) above, the R group is one factor influencing the Diels-Alder polymerization and the homopolymerization temperatures. In general, when R is a hydrogen atom in monomers of the formula (I) above, Diels-Alder polymerization of the monomers occurs at a temperature greater than about 200° C., while homopolymerization of the ethynyl group occurs at a temperature greater than about 170° C. Preferably, when R is a hydrogen atom in monomers of the formula (I) above, Diels-Alder polymerization of the monomers occurs at a temperature of about 200° to 350° C., while homopolymerization of the ethynyl group occurs at a temperature of about 170° to 250° C. Because homopolymerization tends to occur at temperatures lower than Diels-Alder polymerization, these monomers are not preferred.

In general, when R is an aryl group in monomers of the formula (I) above, Diels-Alder polymerization of the monomers occurs at a temperature of about 200° C. to 350° C., while homopolymerization of the phenylethynyl group occurs at a temperature of greater than about 350° C.

A Differential Scanning Calorimetric Study (DSC) indicates the endothermic or exothermic nature of a reaction as the temperature is increased. Typically, the reaction temperature is plotted on the abscissa while the amount of heat absorbed or evolved is plotted on the ordinate. A DSC study is useful in the present invention because it indicates the Diels-Alder polymerization and homopolymerization exotherms for a given monomer. For example, when L is represented by the formula (VI) where B is a condensed benzene ring and Q is a direct bond, and R is a hydrogen atom, the DSC is represented by FIG. 1 which was run at a heating rate of 10° C./min. FIG. 1 shows a melting temperature of about 198° C. and two reaction exotherms, 202° C. and 269° C. The first exotherm relates to the homopolymerization while the second exotherm relates to the in situ generation of the o-xylylene at 269° C.

In another example, when L is represented by the formula (VI) where B is a condensed benzene ring, Q is a direct bond, and R is a phenyl group, the DSC is represented by FIG. 2. FIG. 2 shows a melting temperature of 196° C. and a single reaction exotherm which encompasses the formation of o-xylylene and its subsequent Diels-Alder addition.

Table 5 sets forth the thermal properties of monomers of the formula (I).

TABLE 5

THERMAL PROPERTIES OF MONOMERS OF FORMULA I

| Example | $T_g$ | $T_m$ | Tpoly Onset | Tpoly Max. | $T_g$ (cure) |
|---|---|---|---|---|---|
| 4 | — | 198 | 170 | 202 | 380$^a$ |
|   |   |   |     | 270 | (380)$^b$ |
| 2 | — | 196 | 209 | 263 | 278$^a$ |
|   |   |   |     |     | (294)$^b$ |
| 10 | — | 200 | 229 | 263 | 215$^a$ |
|    |   |   | 321 | 372 |   |
| 9 | 102 | 238 | 238 | 266 | 380$^a$ |
|   |     |     | 298 | 347 | (416)$^b$ |

All Table 5 temperature values are expressed in ° C. The monomers are identified by reference to the examples given below. Tg is the glass transition temperature of the monomer while Tm is the melting temperature of the monomer. Tpoly onset is the temperature at which polymerization begins while Tpoly max is the temperature of the exotherm maximum in DSC analysis. The Tg, Tm and Tpoly values were obtained by subjecting monomer samples to DSC measurements, which indicate the amounts of heat absorbed (endothermic) or evolved (exothermic) with respect to a reference temperature point or range when the sample undergoes either physical changes (Tg, Tm) or chemical changes (Tpoly).

Tg(cure) is the glass transition temperature of the cured monomer. Tg(cure) was determined both by DSC analysis (value a) and by thermomechanical analysis (value b) which employ a sensitive probe to detect the softening of the sample at its surface. Because Tg(cure) relates to the cured material, all cured samples were obtained by subjecting the monomers to an eight hour heat treatment at 250° C. and another eight hour heat treatment at 350° C. under nitrogen atmosphere.

FIG. 3 provides isothermal aging studies of cured samples of monomers of formula (I). The samples were cured as indicated above for Tg(cure). The Example numbers correspond to the examples given below. The isothermal aging studies were carried out by placing samples of the cured monomer in a circulating air oven for 200 hours, and periodically measuring the change in weight. This data illustrates the high temperature utility of the resins of the present invention.

The Diels-Alder polymerization of the monomers has a significant impact on the nature and properties of the resins prepared. In one embodiment, the resins are useful as adhesives. In a preferred embodiment, resins prepared by the Diels-Alder polymerization of monomers of the formula (I) above where L is a benzimido group represented by the formula (VIa) above are high-temperature tolerant thermoset resins useful in composites and as adhesives.

The present invention is illustrated in more detail by the following non-limiting examples which show the preparation of monomers useful in the present invention:

EXAMPLES 1

Preparation of N-4-benzocyclobutenyl 4-bromophthalimide

A mixture of 4-bromophthalic anhydride (12.4 g, 54.6 mmoles) and 4-amino-benzocyclobutene (6.5 g., 54.5 mmoles), freshly prepared from the catalytic hydrogenation of 4-nitro-benzocyclobutene, were gently refluxed in glacial acetic acid (120 ml) under nitrogen atmosphere for about 17 hrs. The resultant dark but homogeneous reaction mixture was allowed to cool to room temperature under $N_2$ and then poured into approximately 750 ml of $H_2O$. Precipitation of gray solid immediately took place. Then, about 200 ml of $CH_2Cl_2$ was added to the mixture to deliver a two-phase, homogeneous solution. Subsequently, the $CH_2Cl_2$ layer was separated and the aqueous layer was extracted further with $CH_2Cl_2$ (2×50 ml). The combined $CH_2Cl_2$ extract was first concentracted to about 100 ml and then passed through a chromotography column (internal diameter, 2 cm., approximately 110 g silica gel, saturated with hexane). Elution of the column with hexane led to the isolations of the desired product, which crystallized out as beige microcrystals upon rotary evaporation. The product was collected, washed with hexane and dried in vacuo at 75° C. overnight. Yield: 11.7 g (65.4%, based on 4-aminobenzocyclobutene). M.P.=167°-168° C. Calculate for $C_{16}H_{10}BrNO_2$: 58.56% C; 3.07% H; 4.27% N; 24.35% Br. Found: 58.03% C; 3.20% H; 4.20% N; 24.26% Br. Mass spectroscopy: 327,329 (31.24%, 35.51%, M+). Proton nmr ($\delta$ values in ppm): 3.24 (singlet; benzocyclobutenyl aliphatic protons, 4); 7.17, 8.06 (complex; aromatic protons, 6H). IR (KBr; in $cm^{-1}$) 2990 vw, 2975 w (aliphatic C—H stretches); 1775 m, 1718 vs (imide linkage stretches).

EXAMPLE 2

Preparation of N-4-benzocyclobutenyl 4-phenylethynylphthalimide

A mixture of N-4-benzocyclobutenyl 4-bromophthalimide (3.75 g, 11.4 mmol), Pd(OAc)$_2$ (20 mg), PPh$_3$ (50 mg) was placed in a 3-necked 100 ml round-bottomed flask equipped with a condenser and a nitrogen adaptor (All glasswares had been baked at 135°-140° C. for approximately 4 hrs., assembled while still hot, and allowed to cool to room temperature under a steady stream of $N_2$.) 55 ml of $NEt_3$, freshly distilled from BaO, was then added to the reaction vessel and the orange, heterogeneous reaction mixture was heated, with continuous stirring, to reflux under $N_2$ for about 30 minutes. Then, the oil bath was removed and phenylacetylene (2.60 g, 25.4 mmol) was added rapidly to the hot reaction mixture through the condenser. Immediately, the quantitative amount of white solid (triethylammonium chloride) precipitated out, and greatly impeded the stirring of the reaction mixture magnetically. Hence, after the reaction vessel had been returned to the oil bath and preheated to about 100° C., approximately 5 ml of $NEt_3$ was added to facilitate stirring. The reaction mixture was gently refluxed for another 3 hrs. and then at approximately 40° C. overnight. Then, the light brown mixture, after allowed to cool to room temperature, was poured into 300 ml $H_2O$. The resultant mixture was extracted with $CH_2Cl_2$ (100 ml, then 3×20 ml). The organic extract was subjected to rotary evaporation to afford 5.17 g of crude brown solid, which was a mixture of the desired product and side products, PhC≡C—C≡C—Ph and PhC≡C—CH=CHPh as suggested by mass spectroscopy. However, column chromatographic purification of the crude product (internal diameter, 2 cm., 30 g silica gel saturated with hexane, and eluting with $CH_2Cl_2$) led to the crystallization of yellow-green microcrystals from the first fractions, after which were added with hexane and subjected to rotary evaporation at room temperature, repeatedly in that manner. Yield=3.63 g (91.2%). m.p.=194-195° C. Calculated for $C_{24}H_{15}NO_2$: 82.50% C; 4.33% H; 4.01% N. Found: 81.78% C; 4.62% H; 4.06% N. Mass spectroscopy: m/e=349 (M+). HPLC purity >96%. Proton nmr ($\delta$ values in ppm): 3.21 (singlet; benzocyclobutenyl alicyclic protons, 4H): 7.31, 8.03 (complex; aromatic protons, 11 H). IR (KBr, in $cm^{-1}$) 2954 w, 2929 vw, 2905 w (alicyclic C-H stretches); 2208 w (—C≡C— stretch); 1769 m, 1695 vs (imide linkage stretch).

EXAMPLE 3

Preparation of N-4-benzocyclobutenyl 4-trimethylsilylethynyl phthalimide

In a 100 ml 3 necked round-bottomed flask, equipped with a thermometer, reflux condenser and $N_2$-adaptor, were placed N-4-benzocyclobutenyl 4-bromophthalimide (4.00 g, 12.2 mmol), palladium acetate (24 mg), triphenylphosphine (48 mg) and 60 ml of dry $NEt_3$. The resultant reaction mixture was refluxed under $N_2$ for about 15 minutes. Then, it was allowed to cool slowly to room temperature under $N_2$. Trimethylsilylacetylene (2.50g, 25.4 mmol) was introduced into the reaction mixture via the reflux condenser. Immediately, the quantitative amount of white solids precipitated. The reaction mixture was then heated at 100° C. for about 3 hrs and stirred at room temperature overnight under $N_2$. The brown heterogeneous mixture was poured into about 300 ml of $H_2O$ and extracted with $CH_2Cl_2$ (2×100 ml+2×50 ml). The $CH_2Cl_2$ extract was then washed with 200 ml $H_2O$ and dried over $MgSO_4$. Upon removal of the solvent, a mixture of white and brown solids was obtained. The mixture was washed with approximately 250 ml of $H_2O$ and air dried for an hour. It was then dissolved in 50 ml $CH_2Cl_2$ and the resultant solution was passed through a short column containing 25 g of silica gel saturated with hexane. Elution with 1:1 $CH_2Cl_2$/hexane led to the isolation of microcrystalline tan solid from the first fraction. Yield=4.0 g (95%) mp=192-193° C. Calc. for $C_{21}H_{19}NO_2Si$: 73.01% C; 5.54% H; 4.05% N. Found: 72.95% C; 5.45% H; 4.01%

N. Mass Spectroscopy: 345 (M+, 100%). Proton NMR (CDCl$_3$) 0.30 (Singlet, Me$_3$Si—); 3.24 (Singlet, alicyclic protons); 7.10–7.29, 7.92–8.06 (complex, aromatic protons). IR(KBr): 2960 m, 2930 m (aliphatic and alicyclic C—H stretches); 2175 w (C≡C stretch); 1712, 1772 (symmetric and asymmetric stretches of imide group).

EXAMPLE 4

Preparation of N-4-benzocyclobutenyl 4-ethynylphthalimide

A mixture of N-4-benzocyclobutenyl 4-trimethylsilylethynyl phthalimide (3.95 g, 11.4 mmol) and potassium carbonate (0.50 g, 3.62 mmol) was stirred in 100 ml of anhydrous methol under N$_2$ at room temperature for about 3 hours. The solvent was then removed, and the residue was treated with 75 ml of H$_2$O and 50 ml CH$_2$Cl$_2$. The methylene chloride layer was separated and the aqueous layer was extracted with CH$_2$Cl$_2$ (2×50 ml). The combined extract was dried over MgSO$_4$, and then filtered through a bed of silica gel (10 g). Slow evaporation of the filtrate led to the isolation of light yellow crystals. Yield: 2.85 g (91%) m.p.=191°–192° . Calc. for C$_{18}$H$_{11}$NO$_2$: 79.10% C; 4.06% H; 5.12% N, Found: 78.98% C; 4.01% H; 5.09% N. Mass Spectroscopy: 273 (M+ 100%). Proton NMR (CDCl$_3$): 3.25 (singlet, alicyclic protons); 3.37 (singlet,≡CH); 7.08–7.31, 7.94–8.08 (complex, aromatic protons). IR(KBr): 3272s (≡CH stretch); 2943m (alicyclic CH stretch); 1710 ms, 1773 vs (symmetric and asymmetric stretches of imide group).

EXAMPLE 5

Preparation of 3-bromophenyl Trimethylsilyl ether

3-Bromophenol (17.3 g, 0.100 mol) and 9 ml of pyridine together with 100 ml of toluene were placed in a 3-necked 250 ml round-bottomed flask equipped with a reflux condensor, an addition funnel and thermometer/adaptor. Chlorotrimethylsilane (12.8 g, 15 ml, 0.12 mol) was added dropwise to the vigorously stirred solution. The resultant white reaction mixture was subsequently refluxed for 4 hrs and then stirred at room temperature overnight. The white precipitate was removed by filtration and the colorless filtrate was subjected to rotary evaporation to remove the solvent. The residual liquid was purified by simple distillation. The pure product was collected at 232°–233° C. Yield: 23.0 g (93%). Calc. for C$_9$H$_{13}$BrOSi: 44.08% C; 5.34% H; 32.59% Br. Found: 43.98% C; 5.36% H; 32.35% Br. Mass Spectroscopy: 244,246 (77%, 78%, M+) Proton NMR ($\delta$ in ppm, CHCl$_3$); 0.27 (singlet, Me$_3$Si—); 6.66–7.32 (complex, aromatic protons).

EXAMPLE 6

Preparation of crude 3-hydroxytolane

Palladium acetate (0.20 g, 8.9×10$^{-4}$ mol) and tri-o-tolylphosphine (0.40 g, 1.31×10$^{-3}$ mol) as well as 60 ml of NEt$_3$ were placed in a 3-necked 100 ml round-bottomed flask equipped with a reflux condensor, a thermometer and a nitrogen adaptor. The resultant yellow mixture was then heated to reflux under N$_2$. At about 70° C., the mixture turned deep-red but still maintained its homogeneity. While the mixture was still refluxing, 3-bromophenyl trimethylsilyl ether (7.10 g, 28.95 mmol) was introduced via the reflux column, allowing it to flow slowly along the wall of the column, into the reaction mixture. After about 15 minutes, degased phenylacetylene (3.11 g, 30.45 mmol) was added to the reaction mixture in a similar manner. As soon as the reactants were in contact, sudden rise in temperature and concomitant precipitation of white solids occurred. The color of reaction mixture became lighter as the reaction progressed. After about 3 hours, the reaction mixture was dark brown and no further change in color was observed even after 17 hours at 80° C. The cooled reaction mixture was poured into about 300 ml of water and extracted with ethyl ether (100 ml, 3×50 ml). The dark ethereal extract was subjected to rotary evaporation to afford a dark oil. About 20 ml of water was added to the dark oil and the mixture was rota-evaporated, in a 70° C-water bath for about 15 minutes. Then, 150 ml of methanol was added and rotary evaporation was resumed until all solvent was removed at 70° C. The resultant dark oil was then dried in vacuo at room temperature for 24 hrs and solidified into dark brown crude product (about 5.0g). Proton NMR (CDCl$_3$): 5.18 (singlet, —OH), 6.71–7.67 (complex, aromatic H). The hydroxyl proton is readily exchanging with deuterium of D$_2$O. IR(KBr): $\delta$ (OH) at 3350 cm$^{-1}$ (strong and broad); $\delta$ (C≡C) at 2210 cm$^{-1}$ (W). The crude product was used in the subsequent reaction without further purification.

EXAMPLE 7

Preparation of N-4-benzocyclobutenyl 4-nitronaphthalimide

A mixture of 4-nitronaphthalic anhydride (2.07g, 8.51 mmol) and 4-aminobenzocyclobutene (1.10g, 0.23 mmol) was stirred in acetic acid (100 ml)/toluene (80 ml) at room temperature for about ½ hr and then heated to reflux under N$_2$. The reaction mixture turned dark and homogeneous upon reflux. The water of imidation was removed azeotropically via a Dean-Stark trap. After about 17 hrs. of reflux, the reaction mixture was cooled to room temperature and poured into about 600 ml of 20% aqueous NaCl solution. After extraction with ethyl acetate until the aqueous layer was almost colorless and clear, the organic extract was washed with saturated NaCl solution (2×500 ml) and then dried over MgSO$_4$. Upon complete removal of the solvent by rotary evaporation, the extract yielded a brown solid as the crude product, which was dissolved completely in CH$_2$Cl$_2$ and filtered through a bed of silica gel (10g), washing with CH$_2$Cl$_2$ until the filtrate was colorless. Complete evaporation of the filtrate led to the isolation of yellow powders. Yield: 2.60g (88.7%). Calc. for C$_{20}$H$_{12}$N$_2$O$_4$: 69.76% C; 3.51% H; 81.38% N. Found: 69.66% C; 3.51% H; 81.24% N. Proton NMR (CDCl$_3$): 3.30 (singlet, alicyclic protons); 7.05–9.04 (complex, aromatic protons). IR(KBr): 2940 w (alicyclic CH stretch); 1720 ms, 1675 vs (carbonyl stretches of imide group); 1530 s, 1350 s (asymmetric and symmetric stretches of nitro group).

EXAMPLE 8

Preparation of N-4-benzocyclobutenyl 4-nitrophthalimide

A mixture of 4-nitrophthalic anhydride (3.46 g, 17.9 mmol) and 4-aminobenzocyclobutene (2.20g, 18.5 mmol) was refluxed in acetic acid under N$_2$ for about 17 hours. The dark reaction mixture was then allowed to cool to room temperature and poured into 500 ml of H$_2$O, followed by extraction with CH$_2$Cl$_2$ (75 ml+3×50 ml). The dark extract was then washed with approximately 300 ml of H$_2$O and then dried over MgSO₄. Complete removal of CH₂Cl₂ from the extract by rotary evaporator afforded a dark oil, which was purified by column chromatography (150 g silica gel; using 1:1 petroleum ether/CH₂Cl₂ as eluent). Pure product was isolated from the first fraction as yellow solid. Yield: 3.21 g (65%). Calc. for C₁₆H₁₀N₂O₄: 65.30% C; 3.42% H; 9.52% N. Found: 65.21% C; 3.39% H; 9.58% N. Mass spectroscopy: 294 (M+, 100%). Proton NMR (CDCl₃): 3.24 (singlet, alicyclic protons). 7.00–7.23, 8.06–8.72 (complex, aromatic protons). IR(KBr): 2900 w, 2770 m, 2650 m (alicyclic C—H stretches); 1720, 1775 (Symmetric and asymmetric stretches of imide group): 1350, 1540 (symmetric and asymmetric stretches of nitro group).

EXAMPLE 9

Preparation of N-4-Benzocyclobutenyl-4-(3-phenylethynyl phenoxy)-naphthalimide

In a 100 ml 3-necked round-bottomed flask were placed 3-hydroxytolane (0.30g, 1.54 mmol), 1.55 ml of standardized (1N) methanolic KOH solution and 65 ml of toluene. The resultant dark-red solution was subjected to simple distillation under N₂. About 55 ml of distillate was collected. After the temperature of the mixture was allowed to cool to about 50° C., dry DMSO (60 ml) was introduced to dissolve completely the dark brown solid formed. The resultant homogeneous, dark solution was distilled again until the head temperature was about 115° C. (pot temperature 145°–150° C.). About an additional 5 ml of toluene was collected. After the dark phenolate solution was allowed to cool to about 35° C. in an oil bath, N-4-benzocyclobutenyl-4 nitro-naphthalic imide (0.53 g, 1.54 mmol) was added next under N₂. The reaction mixture was stirred at 35°–40° C. for about 1½ hour and then allowed to cool to room temperature. After having been poured into a separatory funnel containing 300 ml of H₂O, the mixture was extracted with CH₂Cl₂ (50 ml, then 3×25 ml). The combined extract was then dried over MgSO₄. The volume of dried extract was reduced to about ⅓ its original volume and then passed through a short column containing about 20 g silica gel, saturated with petroleum ether. The column was then eluted with 1:1 petroleum ether/CH₂Cl₂. The collected yellow solution was concentrated and chilled overnight to afford yellow microcrystals. Yield: 0.55 g (77%). m.p.: 235°–236° C. Calc. for C₃₄H₂₁NO₃: 83.08% C; 4.31% H; 2.85% N. Found: 82.97% C; 4.25% H; 2.90% N. Mass Spectroscopy: 491 (M+, 75.7%). Proton NMR (CDCl₃) 3.21 (singlet, alicyclic protons); 6.88–7.89, 8.41–8.72 (complex, aromatic protons). IR(KBr): 2705 m (alicyclic CH stretch); 1710 ms, 1670 vs (symmetric and asymmetric stretches of imide group): 1240 vs. (Ar—0—Ar stretch).

EXAMPLE 10

Preparation of N-4-Benzocyclobutenyl-4-(3-phenylethynyl phenoxy)-phthalimide

In a 100 ml 3-necked round-bottomed flask were placed 3-hydroxytolane (0.69 g, 3.55 mmol), 3.6 ml of standardized methanolic KOH solution (3.60 ml, 3.60 mmol) and 75 ml of toluene. The resultant dark solution was distilled under N₂ until about 65 ml of distillate was collected. After the remaining mixture had been cooled to room temperature, 55 ml of DMSO was added. Distillation was resumed until the head temperature reached about 120° C. (pot temperature: about 150° C.). An additional 7 ml of distillate was collected.

The dark phenolate/DMSO solution was allowed to cool to about 35° C. in an oil bath. N-4-benzocyclobutenyl 4-nitrophthalimide (1.00g, 3.40 mmol) was added next. The resultant reaction mixture was stirred under N₂ at 30°–35° C. for another 2½ hours. Then, the reaction mixture was poured into a separatory funnel containing about 300 ml of H₂O and extracted with ethyl acetate (100 ml, 3×50 ml). The organic extract was then washed with saturated NaCl solution (2×150 ml) and dried over MgSO₄. The volume of the dried extract was concentrated on a rotary evaporator to about 10 ml and passed through a chromatographic column containing about 100 g of silica gel saturated with petroleum ether. Elution was carried out with 100 ml petroleum ether, followed by 1:2 CH₂Cl₂/ petroleum ether. 4 bands were developed in the column. The desired product which was contained in the first band, was isolated as light yellow microcrystals. Yield: 0.45 g (30%). Calc. for C₃₀H₁₉NO₃: 81.62% C; 4.34% H; 3.17% N. Found: 81.05% C; 4.31% H; 3.09% N. Mass Spectroscopy: 441 (M+, 100%). Proton NMR (CDCl₃): 3.20 (singlet, alicyclic protons); 7.00–7.93, (complex, aromatic protons). IR(KBr): 2700 m (alicyclic C—H stretches); 1706 m, 1778 vs (symmetric and asymmetric stretches of imide group): 1238 ms (Ar—O—Ar stretch).

Having described the invention in detail and by reference to preferred embodiments thereof, it will be apparent that modifications and variations are possible without departing from the scope of the invention defined in the appended claims.

What is claimed is:

1. A monomer of the formula

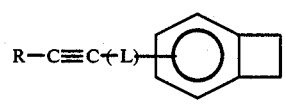

(I)

where

R is a hydrogen atom or an aryl group; and

L is an aromatic linking group.

2. The monomer of claim 1 wherein R is a phenyl group.

3. The monomer of claim 1 wherein said monomer is represented by the formula

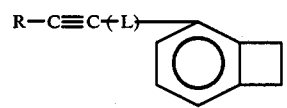

(Ia)

and R and L are defined as in claim 1.

4. The monmer of claim 1 wherein said monomer is represented by the formula

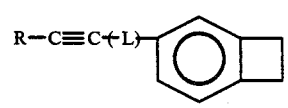

(Ib)

and R and L are defined as in claim 1.

5. The monmer of claim 1 wherein L is represented by the formula selected from the group consisting of

[Structures (II), (III), (IV), (V) shown]

where
- W, X, and Y are a hydrogen atom or a nitrogen atom; and
- Z represents the atoms necessary to complete a nitrogen containing heterocyclic ring.

6. The monomer of claim 5 wherein said nitrogen containing heterocyclic ring is selected from the group consisting of an imidazole ring, an oxazole ring, and a thiazole ring.

7. The monomer of claim 1 wherein L is a benzimido group represented by the formula

[Structure (VI) shown]

where
- B represents the atoms necessary to complete a condensed benzene ring or a condensed naphthalene ring; and
- Q is a direct bond or a moiety of the formula

[Structure (VII) shown]

where n is 1 or 2.

8. The monomer of claim 7 wherein B represents a condensed benzene ring.

9. The monmer of claim 1 wheren L is represented by the formula

[Structure (VIII) shown]

where T is selected from the group consisting of $$-\overset{O}{\underset{\parallel}{C}}-, -\overset{O}{\underset{\parallel}{C}}-O-, -\overset{O}{\underset{\parallel}{C}}-NH-, -O-, \text{ and } -SO_2-.$$

10. The monomer of claim 1 wherein L is represented by the formula

[Structure (IX) shown]

where M is selected from the group consisting of $-C(CF_3)_2-$, $-C(CH_3)_2-$, and $$-\overset{O}{\underset{\parallel}{C}}-.$$

11. The monomer of claim 1 wherein L is represented by the formula

[Structure (X) shown]

where P is selected from the group consisting of $-SO_2-$, $-C(CF_3)_2-$, and $-C(CH_3)_2-$.

12. A resin which is a reaction product prepared by Diels-Alder polymerization of monomers of the formula

[Structure (I) shown: R—C≡C—(L)—phenyl ring fused]

where
- R is a hydrogen atom or an aryl group; and
- L is an aromatic linking group.

13. The resin of claim 12 wherein R is a phenyl group.

14. The resin of claim 12 wherein said monomer is represented by the formula

[Structure (Ia) shown]

and R and L are defined as in claim 12.

15. The resin of claim 12 wherein said monomer is represented by the formula

[Structure (Ib) shown]

and R and L are defined as in claim 12.

16. The resin of claim 12 wherein L is represented by the formula selected from the group consisting of

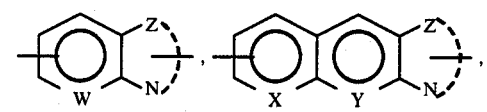

(II)    (III)

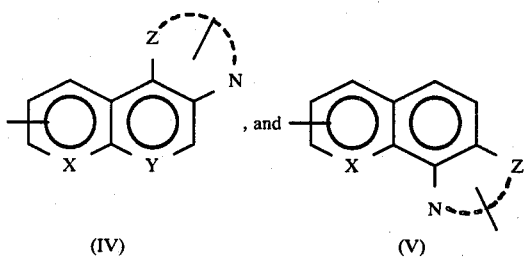

(IV)    (V)

where
W, X, and Y are a hydrogen atom or a nitorgen atom; and
Z represents the atoms necessary to complete a nitrogen containing heterocyclic ring.

17. The resin of claim 16 wherein said nitrogen containing heterocyclic ring is selected from the group consisting of an imidazole ring, an oxazole ring, or a thiazole ring.

18. The resin of claim 12 wherein L is a benzimido group represented by the formula

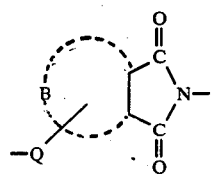

(VI)

where
B represents the atoms necessary to complete a condensed benzene ring or a condensed naphthalene ring; and
Q is a direct bond or a moiety of the formula

(VII)

where n is 1 or 2.

19. The resin of claim 18 wherein B represents a condensed benzene ring.

20. The resin of claim 12 wherein L is represented by the formula

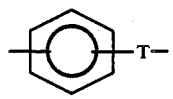

(VIII)

where T is selected from the group consisting of

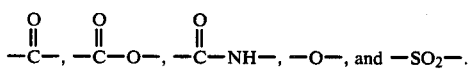

21. The resin of claim 12 wherein L is represented by the formula

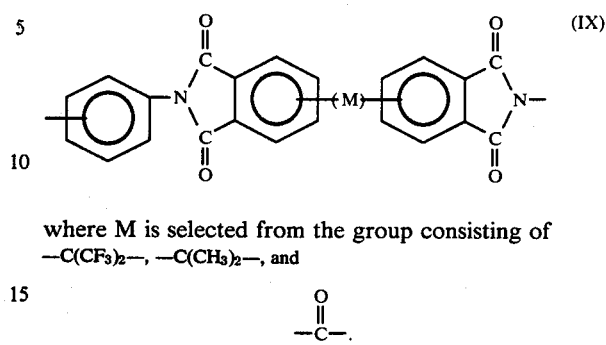

(IX)

where M is selected from the group consisting of
—C(CF$_3$)$_2$—, —C(CH$_3$)$_2$—, and $$\underset{\underset{O}{\overset{\|}{-C-}}}{}$$

22. The resin of claim 12 wherein L is represented by the formula

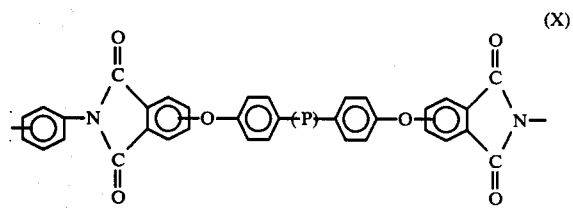

(X)

where P is selected from the group consisting of —SO$_2$—, —C(CF$_3$)$_2$—, and —C(CH$_3$)$_2$—.

23. The resin of claim 12 wherein said resin is prepared by heating said monomer to a temperature at which said Diels-Alder polymerization of said monomers occurs at a substantially greater rate than homopolymerization of said alkynyl group.

24. The resin of claim 12 wherein said monomer is heated to a temperature less than about 360° C.

25. A process for preparing resins which comprises heating monomers of the formula

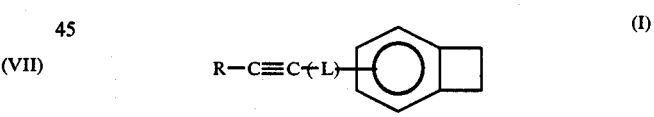

(I)

where
R is a hydrogen atom or an aryl group; and
L is an aromatic linking group to a temperature at which Diels-Alder polymerization of said monomers occurs at a substantially greater rate than homopolymerization of said alkynyl group.

26. The monomer of claim 1 wherein L is a benzimido group represented by the formula

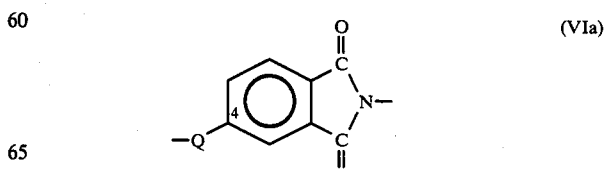

(VIa)

where Q is a direct bond or a moiety of the formula

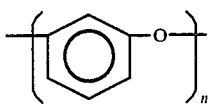
where n is 1 or 2.
27. The resin of claim 12 wherein L is a benzimido group represented by the formula
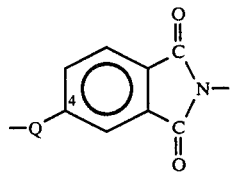
(VIa)
where Q is a direct bond or a moiety of the formula
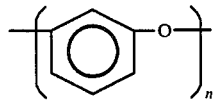
(VII)
where n is 1 or 2.
* * * * *

UNITED STATES PATENT AND TRADEMARK OFFICE
CERTIFICATE OF CORRECTION

PATENT NO. : 4,675,370

DATED : June 23, 1987

INVENTOR(S) : Loon-Seng Tan et al.

It is certified that error appears in the above-identified patent and that said Letters Patent is hereby corrected as shown below:

Column 3, line 48, "necessayr" should read -- necessary --.

Column 3, line 50, "consistng" should read -- consisting --.

Column 18, lines 57 and 67, and Column 19, line 55, "monmer", each occurrence, should read -- monomer --.

Column 21, line 21, "nitorgen" should read -- nitrogen --.

Signed and Sealed this

Twelfth Day of April, 1988

Attest:

DONALD J. QUIGG

Attesting Officer

Commissioner of Patents and Trademarks